United States Patent [19]

Lieb et al.

[11] 4,313,725
[45] Feb. 2, 1982

[54] DENTAL HANDPIECE AND COLLET WRENCH THEREFOR

[75] Inventors: Nathaniel H. Lieb, Narberth; Albert D. Alderman, Jr., Skippack; James L. Alago, Lansdale, all of Pa.

[73] Assignee: Venture Technology, Inc., West Conshohocken, Pa.

[21] Appl. No.: 147,696

[22] Filed: May 7, 1980

[51] Int. Cl.³ ............................................. A61C 1/08
[52] U.S. Cl. .................................... 433/126; 81/55; 81/462
[58] Field of Search ............. 433/126, 129; 279/1 SG, 279/1 Q; 81/52.4 R

[56] References Cited

U.S. PATENT DOCUMENTS

| | | | |
|---|---|---|---|
| 3,324,553 | 6/1967 | Borden | 433/126 |
| 3,325,899 | 6/1967 | Staunt | 433/129 |
| 3,400,459 | 9/1968 | Stemler | 433/129 |
| 3,499,223 | 3/1970 | Lieb et al. | 433/129 |
| 3,731,384 | 5/1973 | Brooks | 433/132 |
| 3,871,097 | 3/1975 | Melde | 433/120 |
| 3,893,242 | 7/1975 | Lieb et al. | 433/127 |
| 3,960,039 | 6/1976 | Nash et al. | 433/126 |
| 4,015,489 | 4/1977 | Lieb et al. | 81/55 |
| 4,198,754 | 3/1980 | Lares | 433/129 |

FOREIGN PATENT DOCUMENTS 643140 9/1950 United Kingdom ................ 433/129

*Primary Examiner*—Robert Peshock
*Attorney, Agent, or Firm*—Caesar, Rivise, Bernstein & Cohen, Ltd.

[57] ABSTRACT

An air driven dental handpiece having an air turbine at one end thereof. Collet means for securing a dental bur therein are positioned within the air turbine. The collet means includes a plurality of collapsible jaws at the bottom thereof. Threads are provided on the exterior surface of the collet means in the area of the jaws. The bottom of the collet means is tapered, and a collet nut is threadedly secured on the collet means. The collet nut has an internal taper which is complementary to the taper of the collet means. The threaded advancement of the collet nut on the collet means causes the collapsing of the jaws of the collet means, through the mating tapers, and accordingly a dental bur can be secured in the collet means.

19 Claims, 9 Drawing Figures

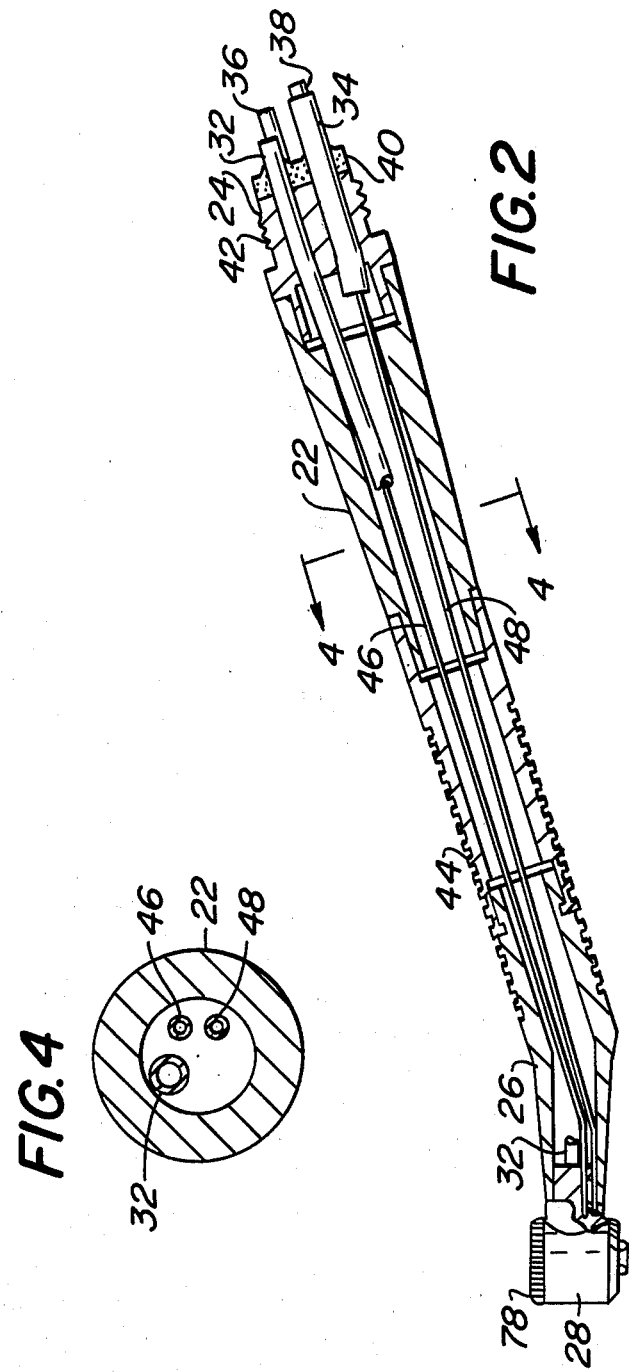

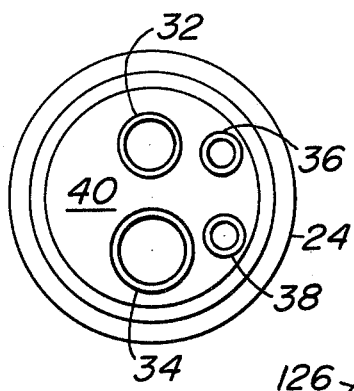
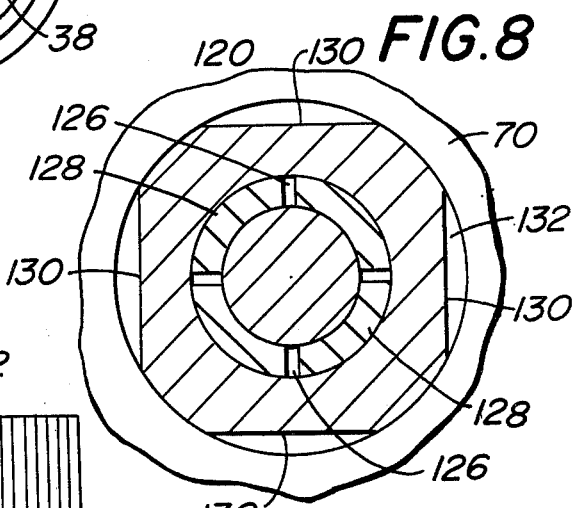
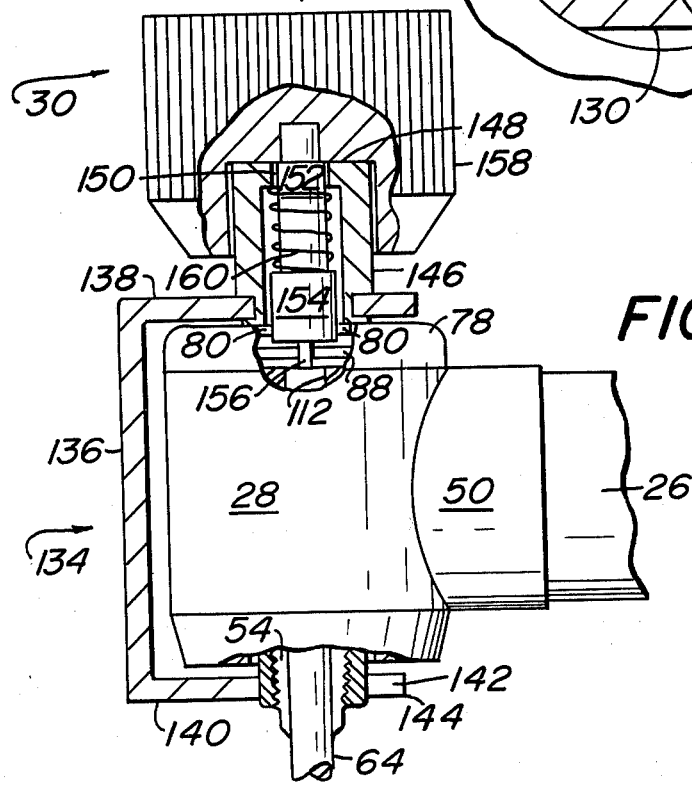

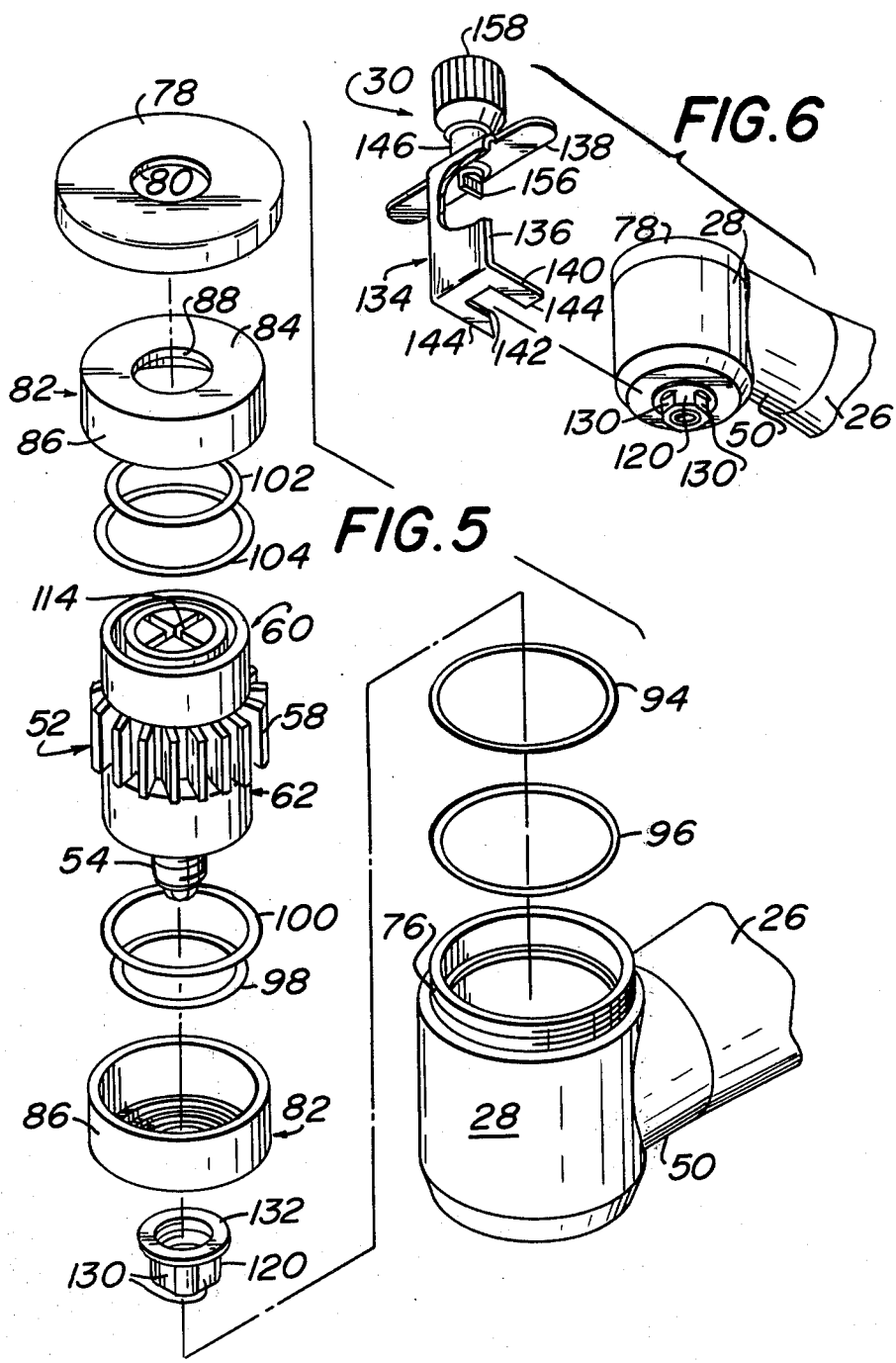

DENTAL HANDPIECE AND COLLET WRENCH THEREFOR

This invention relates to a dental handpiece, and more particularly, to a novel air driven dental handpiece that includes a novel collet assembly and a wrench therefor.

It is now common practice in the dental art to supply rotative power to a dental handpiece through the use of an air driven rotor or turbine. Extremely high speeds have been attained utilizing pneumatically driven dental handpieces. One of the problems that developed in the early air driven dental handpieces related to the collet used for securing the bur within the handpiece. The collets originally used comprised an elastic sleeve formed from rubber or plastic. A problem with this type of collet is that there is not a positive lock or securement on the dental bur, and it was found that the dental bur could work loose during use of the handpiece, or would not rotate concentrically.

The first improvement on the collet for an air driven dental handpiece is that disclosed in U.S. Pat. No. 3,120,706. In this patent, a collet is threadedly secured within the rotor shaft. The collet is rotated relative to the shaft in order to insert a bur and lock it in place, or in order to remove the bur. In this patent, the rotor is prevented from rotating by a finger that is inserted through the turbine housing into the rotor blades while a hexagonal wrench is inserted in the upper end of the collet in order to rotate the collet.

Various improvements have been made in wrenches used for locking the rotor shaft while permitting the threading of the collet relative to the rotor shaft. Examples of these improvements are seen in U.S. Pat. Nos. 3,325,899, 3,499,223 and 4,015,489. In all of these improvements, the collet is still threadedly connected to the rotor shaft, and the means for preventing rotation of the rotor shaft while threadedly advancing or retracting the collet enters the handpiece from the top or rear side thereof.

The collet assembly of this invention provides a distinct advantage over all of the prior threaded collet assemblies. In the collet assembly of this invention, the collet is rigidly connected to the rotor, and does not move relative thereto. Although a threaded mechanism is used for collapsing the collet jaws, this mechanism is a collet nut threadedly secured to the bottom of the collet. Only the collet nut will move in closing the collet jaws, and the collet will remain stationary. The structure of the collet assembly of this invention is economical, easily manufactured and easily serviced.

The invention also includes a collet wrench to be used in combination with the handpiece of this invention. The collet wrench is easily used in opening and closing the collet for inserting, securing and removing a dental bur.

There are also disclosed in this application a novel mounting for the air turbine and a novel water spray system. These aspects of the disclosure are covered in co-pending Application Ser. No. 144,107, filed Apr. 28, 1980 and entitled "HANDPIECE".

It is accordingly an object of this invention to provide a novel dental handpiece.

It is another object of this invention to provide a dental handpiece having a novel collet assembly.

It is a further object of this invention to provide a dental handpiece having a novel collet assembly and a wrench used in combination therewith.

These and other objects of this invention are accomplished by providing a dental handpiece comprising a turbine housing, a turbine rotatably mounted therein, and a collet secured within said turbine, said collet having a plurality of jaws at the bottom thereof, said collet being externally threaded in the area of said jaws, a collet nut threadedly secured on said collet at said threads, said collet being exteriorly tapered at the bottom thereof, said collet nut being internally tapered, with the taper of said collet nut complementing the taper on said collet, and means for rotating said collet relative to said collet nut whereby the advancing of said collet nut on said collet causes the compressing of said collet jaws through the pressure of the mating of said tapered surfaces.

Other objects and many of the attendant advantages of this invention will be readily appreciated as the same becomes better understood by reference to the following detailed description when considered in connection with the accompanying drawings wherein:

FIG. 2 is a partial sectional view of the handpiece of FIG. 1;

FIG. 3 is an end elevational view taken in the direction of line 3—3 of FIG. 1;

FIG. 4 is an enlarged sectional view taken along the line 4—4 of FIG. 2;

FIG. 5 is an exploded perspective view of the elements contained within the turbine housing of the handpiece of this invention;

FIG. 6 is a exploded perspective view of the wrench and turbine housing of the handpiece of this invention;

FIG. 8 is an enlarged sectional view taken along the line 8—8 of FIG. 7; and,

FIG. 9 is a side elevational view, partially in section, showing the mounting of the wrench on the handpiece of this invention.

Figure 1:
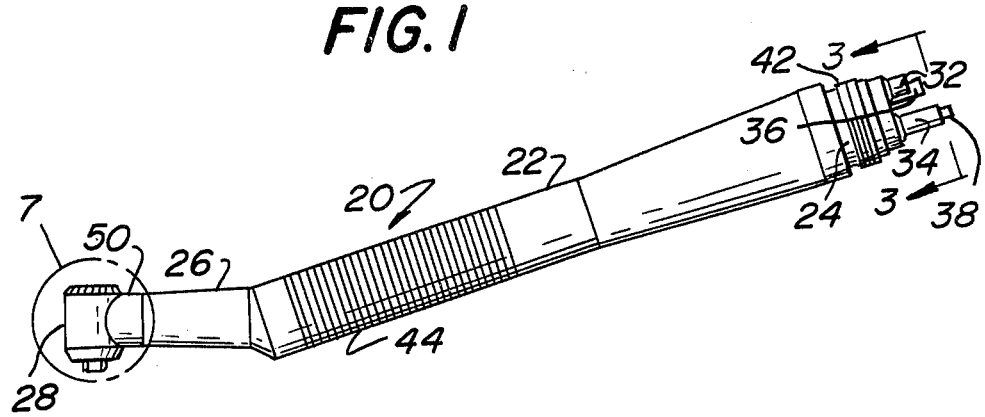
FIG. 1 is a side elevational view of the handpiece of this invention.

Referring now in greater detail to the various figures of the drawings wherein like reference characters refer to like parts, an air driven dental handpiece embodying the present invention is generally shown at 20 in FIG. 1. Device 20 basically comprises a hollow handle 22 and an adaptor block 24 at the rear end thereof. Handle 22 includes an angled neck 26 at the front end thereof, and a turbine housing 28 is mounted on neck 26. A wrench used in connection with the chucking mechanism of the turbine is generally shown at 30 in FIG. 6, and will be described in further detail hereinafter.

As best seen in FIG. 2, adaptor block 24 is secured in the end of hollow handle 22, as by a pressed fit. Passing through the adaptor block 24 is an air inlet tube 32 and an air exhaust tube 34. Tube 32 supplies the driving air for the turbine. A water tube 36 and an air tube 38 also pass through adaptor block 24. Water tube 36 provides coolant water for the bur and air tube 38 serves the dual function of aspirating the water and serving as a chip blower. Suitable controls, well known to the art, regulate the use of the air passing through tube 38 for either function. A rubber or plastic cushion 40 surrounds all the tubes passing through the adaptor block 24.

External connections are made with the various tubes passing through adaptor block 24 through the use of an adaptor nut, which is well known to the art. The adaptor nut is secured on the adaptor block 24 through threads 42 on the adaptor block. The adaptor nut provides gasketed connections with tubes 32, 34, 36 and 38 to provide incoming air and water. If desired, exhaust tube 34 can be exhausted to the atmosphere through the adaptor nut. The connection of the adaptor nut on the adaptor block is well known to the art, and is not illustrated herein.

Handle 22 is provided with a plurality of spaced, annular grooves 44 in the surface thereof. These grooves aid in the grasping of the handle 22, in a manner well known to the art. Water tube 36 is connected to a smaller diameter tube 46 within adaptor block 24. Similarly, air tube 38 is connected to a smaller diameter tube 48 within the adaptor block.

Figure 7:
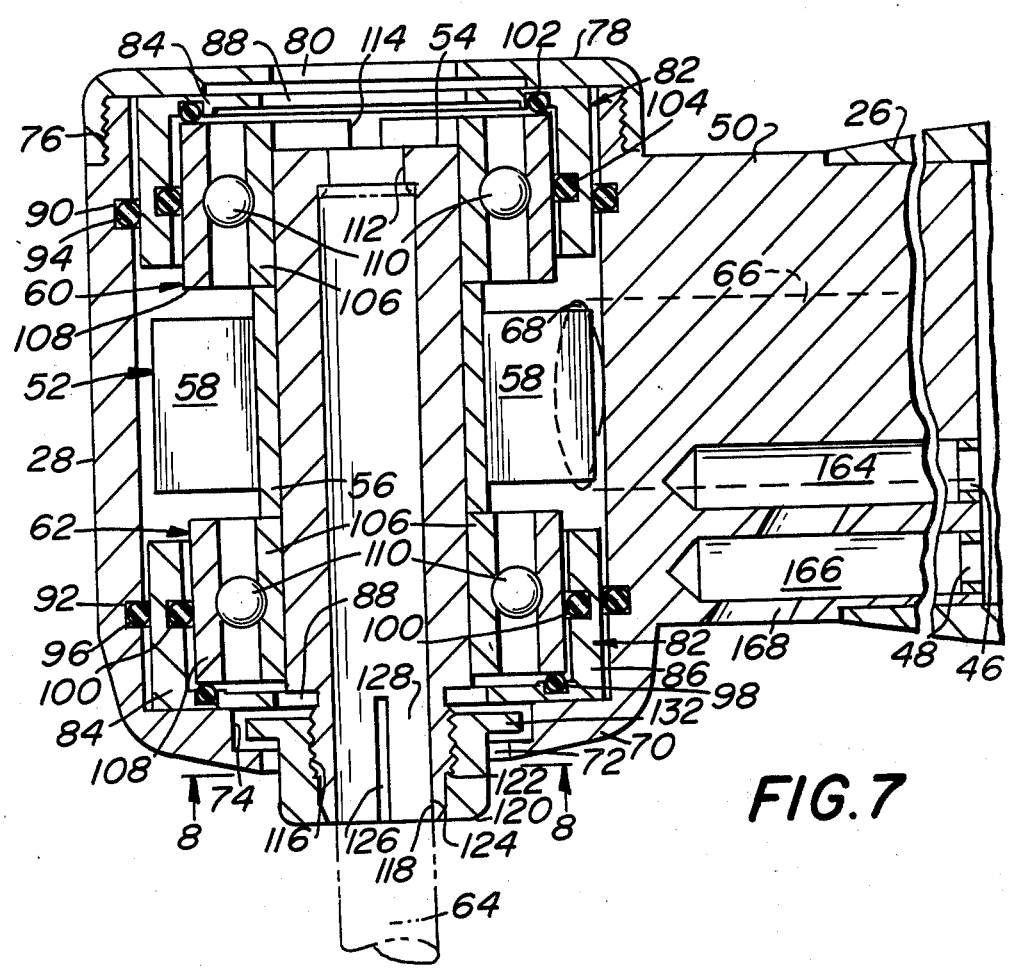
FIG. 7 is an enlarged sectional view taken in the area 7 of FIG. 1.

Referring to FIG. 7, it is seen that turbine housing 28 includes an extension 50. Extension 50 is received within neck 26, and secured therein, as by a pressed fit or welding. Mounted within turbine housing 28 is turbine cartridge 52. Turbine cartridge 52 comprises a collet 54, a rotor hub 56 secured thereon, rotor blades 58 integral with hub 56, upper ball bearing 60 and lower ball bearing 62.

In the operation of the handpiece, a dental bur 64 is secured in collet 54, in the manner described hereinafter. Air to drive the turbine is then furnished, via suitable controls, through tube 32 (FIG. 2). The tube 32 terminates in extension 50 of turbine housing 28 (FIG. 7), where it enters conduit 66 in the extension. Conduit 66 terminates in the wall of turbine housing 28 at opening 68. The impingement of the air exiting from opening 68 against rotor blades 58 causes the turbine to rotate within the turbine housing. Since the collet 54 is secured to the rotor hub, it will rotate therewith, thereby rotating the bur 64. Exhaust air passes through a second conduit (not shown) in extension 50, through the hollow handle 22, and exhausts through tube 34 (FIG. 2). The exhaust conduit is adjacent conduit 66, and has the same size as conduit 66.

To the extent desired, the handpiece of this invention is basically the same in structure and function as the prior art handpieces. Thus, substantially all of the prior art handpieces rely on the same basic combination of elements to supply air to a turbine to obtain rotative power for a dental bur. The improvements of this invention relate to the collet assembly and the wrench 30 used therewith.

Turbine housing 28 is circular in interior cross-section, as best seen in FIG. 5. As seen in FIG. 7, the turbine housing includes a unitary bottom wall 70. A central opening 72 is formed in bottom wall 70. Wall 70 includes an annular interior recess 74. The upper end of turbine housing 28 is open, and includes exterior threads 76 (FIGS. 5 and 7) thereon. An end cap 78 is threadedly secured on turbine housing 28, and closes the same. As seen in FIG. 2, end cap 78 has surface grooves thereon to aid in securing the same in place. End cap 78 is provided with a central opening 80.

The elements mounted within turbine housing 28 in the assembled condition of the handpiece are best seen in FIG. 5. As seen therein, the turbine cartridge 52 comprising the collet, rotor and blades, and ball bearings is shown as a preassembled unit. A pair of isolator members 82 are provided. Each isolator member 82 includes a base disc 84 and a peripheral, unitary wall 86. Each disc 84 includes a central opening 88.

Referring to FIG. 7, it is seen that turbine housing 28 has an upper annular groove 90 and a lower annular groove 92 formed in the interior wall thereof. A rubber O-ring 94 is placed in upper groove 90 and rubber O-ring 96 is placed in lower groove 92. In assembling the handpiece, lower isolator 82 is first placed within turbine housing 28, the rests on bottom wall 70 of the housing. A rubber O-ring 98 is placed within a groove of the disc 84 of the lower isolator, and a rubber O-ring 100 is placed within a groove in the wall 86 of the lower isolator. With the lower isolator in place, the turbine cartridge 52 is then inserted into the turbine housing.

A rubber O-ring 102 is inserted in a groove in the disc 84 of upper isolator 82, and a rubber O-ring 104 is inserted in a wall 86 of the upper isolator 82. Thereafter, the upper isolator, with the O-rings in place, is placed on top of the upper ball bearing 60 (FIG. 7). Once the upper isolator has been inserted in place, the end cap 78 is screwed on the turbine housing 28, thereby completing the structure shown in FIG. 7.

As seen in FIG. 7, each of bearings 60 and 62 comprises an inner race 106, an outer race 108 and balls 110 positioned between the races. The inner races 106 are secured to collet 54 by a pressed fit, and accordingly rotate along with the collet and the rotor. The outer races 108 remain stationary during rotation.

It is thus seen that the isolators 82 and their associated rubber O-rings provide a total resilient mounting for the turbine cartridge. The isolators are resiliently mounted against the O-rings 94 and 96. The outer races 108 are resiliently mounted against the O-rings 98, 100, 102 and 104. It is this resilient mounting for the turbine cartridge that provides for the sound dampening, increased bearing life and vibration dampening of the handpiece. This feature of the handpiece is covered by aforementioned Application Ser. No. 144,107.

Referring to FIG. 7, it is seen that collet 54 has an opening 112 at the top thereof. A crosscut is made in the top of collet 54 at opening 112, thereby forming slots 114 (see also FIG. 5). The bottom of collet 54 is externally threaded, as seen at 116 in FIG. 7. Below threads 116, the exterior wall of collet 54 is tapered inwardly, as shown at 118.

A collet nut 120 is threadedly secured on collet 54. The rotation of the collet relative to the collet nut raises and lowers the nut on the collet. A rim 122 is formed on the collet nut which abuts a similar rim on the collet. This limits the upward movement of the nut relative to the collet. The interior surface of the collet nut is inwardly tapered, as shown at 124. The taper 124 is complementary with the taper 118 of the collet. Collet 54 has a hollow bore, and four equally-spaced slots 126 are formed therein, thereby forming jaws 128 (see also FIG. 8).

Collet nut 120 has four equally spaced flattened surfaces 130 on the exterior surface thereof (see FIGS. 5 and 8). Collet nut 120 further includes an annular flange 132 projecting from the top thereof (FIGS. 5 and 7). The flange 132 is received within recess 74 of bottom wall 70 of turbine housing 28.

The wrench 30 and its function are best seen in FIGS. 6 and 9. The wrench includes a bracket 134 comprising a vertical wall 136, a top wall 138 and a bottom wall 140. Bottom wall 140 includes a central slot 142, thereby forming a pair of jaws 144. A tube 146 (FIG. 9), having an annular groove adjacent the bottom thereof, is snapped into an opening in top wall 138 of bracket 134, thereby securing the tube in place. Tube 146 has an integral top wall 148 having a central opening 150 therein. A rod 152 passes through opening 150. Rod 152 has a hub 154 adjacent the bottom thereof. The bottom of rod 152 terminates in a flat blade 156 (FIGS. 6 and 9).

The top of rod 152 is secured in a knob 158, as by a pressed fit (FIG. 9). As seen in FIGS. 6 and 9, knob 158 has surface grooving to aid in grasping the same. A compression spring 160 is telescoped over rod 152, and has one end abutting the undersurface of top wall 148 of tube 146 and the other end abutting the top of hub 154.

The wrench 30 is used for inserting or removing the dental bur 64 from the handpiece. When it is desired to utilize the wrench, the knob 158 is first raised, thereby raising the rod 152. The movement of the knob is indicated by arrow 162 in FIG. 9. When the knob 158 is raised, spring 160 will be compressed, and blade 156 of rod 152 will be within the confines of tube 46. At this time, the bracket 134 can be slid over turbine housing 28. A pair of flattened faces 130 of collet nut 120 are received in slot 142 and between jaws 144 of bracket 134. This secures the collet nut 120 in place, and prevents any rotation of the same.

Once the collet nut has been secured in place, knob 158 is released, thereby expanding spring 160. The knob 158 is rotated until blade 156 is received in a pair of aligned slots 114 (FIG. 5) in the top of the collet. The position of the blade 156 in the slots is shown in FIG. 9. Once the blade is in place, knob 158 is rotated. If the knob 158 is rotated in a counterclockwise direction, as viewed in FIG. 9, the collet nut 120 will be lowered relative to collet 54. Thus, since the collet is threadedly secured to the collet nut, as seen in FIG. 7, the rotating of the collet relative to the nut in a counterclockwise direction will tend to unthread the nut relative to the collet. When this is done, the pressure of tapered wall 124 of the collet nut against the tapered wall 118 of the collet will be removed, since these tapered walls will be separated. This permits the expansion of the jaws 128 of the collet about slots 126 (FIG. 8).

Once the jaws have been expanded, the dental bur 64 can be removed from the collet. The insertion of the dental bur is carried out by following the same procedure with the collet wrench 30. Thus, once the dental bur 64 has been inserted in the collet and the wrench is in the position shown in FIG. 9, the knob 158 is rotated in a clockwise direction. This in turn will rotate the rod 152, thereby rotating the collet 54 in which the blade 156 is engaged. When rotating in this direction, the collet nut 120 will be threadedly advanced relative to the collet 54, until the tapered wall 124 of the collet nut abuts the tapered wall 118 of the collet. Further advancement of the collet nut causes the jaws 128 of the collet to compress under the urging of the mating tapered walls. As the walls are compressed, the bur 64 will be held securely in place. It should be noted that the knob 158 and rod 152 are rotatable relative to tube 146 which is secured to bracket 134. The jaws 144 of the bracket prevent any rotation of the collet nut during the time that the collet is being rotated.

The threaded securement of the collet relative to the collet nut provides a positive grip on the dental bur, and insures concentric rotation of the dental bur during use of the handpiece. Utilizing the prior art resilient collets it has been found that the rotation of the dental bur can become non-concentric due to compression of the collet during the drilling of a tooth. This make drilling of the tooth more difficult, and can result in inaccurate or improper drilling.

One of the features of the collet and collet nut arrangement is the provision of the shoulder 122 on the collet nut and the adjacent shoulder on the collet. Thus, once the collet nut has been tightened to the position shown in FIG. 7, further tightening is prevented by the abutment of the two shoulders. This prevents the collapsing and breaking of the collet jaws if the dentist should inadvertently start to tighten the collet with no bur inserted therein.

Another feature of the collet nut is the provision of flange 132. If the dentist should inadvertently rotate the collet in a counterclockwise direction to too great an extent, it might be possible to totally remove the collet nut from the collet. If this should occur, the dentist might lose the collet nut, thereby rendering the handpiece unusable. However, having the flange 132 and further having the opening 72 of a smaller diameter then the diameter of the flange 132, if the dentist should inadvertently tend to overloosen the collet, the bottom wall of the flange 132 will contact the bottom wall 70 of the turbine housing 28, thereby preventing any further rotation of the collet. This will insure that the collet nut will never be removed from its threaded securement on the collet.

As an alternate embodiment, the opening 72 can be greater than the diameter of flange 132. In this case, the unthreading of the collet nut relative to the collet will be terminated when the flange 132 abuts the upper surface of the bottom wall 140 of bracket 134. In this case, the bottom wall of the bracket will prevent any further rotation of the collet.

It should be noted that during the rotation of the collet, all of the movable elements within the turbine housing will also rotate. Thus, the rotor and the inner races of the ball bearings will also rotate. The collet will remain at its fixed position within the handpiece, and the only movement will be that of the collet nut in a vertical direction. Thus, even though it is the collet that is being rotated, only the nut will move. The jaws 144 of the bracket 134 prevent the collet nut from rotating during the rotation of the collet, but the slot 142 is sufficiently wide to permit the collet nut to move vertically therein when the collet is being rotated.

Another feature of the handpiece is the coolant spray system. This feature is being described herein solely for the purpose of completeness. It should be understood that this feature is the subject of a separate invention which is covered by aforementioned Application Ser. No. 144,107.

It has been found that the use of the high speed air driven dental handpieces has created a problem, namely, the generation of large amounts of frictional heat in a tooth that is being drilled. It has therefore become necessary to cool the tooth during the drilling thereof. The method of cooling which is almost exclusively used is that of directly supplying a water spray against the tooth while the drilling is being carried out.

Various spray devices have been developed for directing water against the tooth being drilled. Some of these spray devices are disclosed in U.S. Pat. Nos. 3,120,706, 3,199,196, 3,499,223 and 4,015,489. In most of these patents, and in the devices currently in use, the mixing of the air and water to provide a coolant spray takes place externally of the handpiece. Generally, the water and air are supplied from separate tubes, and are mixed after exiting from these tubes. Although U.S. Pat. No. 3,199,196 does disclose the mixing of air and water prior to the mixtures exiting the spray tubes, in this patent the spray is generated in an external device surrounding the dental bur. In the handpiece of this application, all mixing of the air and water occurs internally within the handpiece. Having the internal mixing prevents any interference by external spray tubes adjacent the dental bur. Furthermore, the external spray tubes can interfere with the dentist's viewing the tooth that is being drilled.

Referring now to FIG. 2, it is seen that the incoming coolant water enters the handpiece through tube 36 and passes through tube 46. As seen in FIG. 7, tube 46 terminates in extension 50 and enters bore 164 in the extension. Similarly, the coolant air to be mixed with the water enters the handpiece through tube 38 and passes through tube 48 within the handpiece. As seen in FIG. 7, tube 48 terminates in extension 50, and the air enters bore 166 in the extension. Bore 164 is in fluid communication with bore 166 via bore 168, which passes through bore 166 and into bore 164. Bore 168 is also in fluid communication with the exterior of the handpiece.

During the operation of the handpiece 20, air for driving the turbine enters the handpiece through tube 32, and drives the turbine in the manner described above. At the same time the air is admitted through tube 32, water is admitted through tube 36 and the coolant air enters through tube 38. The water ultimately enters bore 164 (FIG. 7) and exits from the bore 164 into bore 168. At this point, the water mixes with the air which is entering bore 166. The air aspirates the water, and the mixture of air and water exits from the handpiece through the bottom of bore 168. In view of the fact that the bore 168 is angled toward the bur 64, the air and water mixture will completely surround the bur and the area of the tooth that is being drilled.

In the prior art external spray systems, wherein the air and water are supplied by separate tubes, and are not mixed until they exit their respective tubes, the water is dispersed against the tooth in relatively large droplets. The premixing of the air and the water in the handpiece of this invention creates a very fine mist or fog of coolant water. The water droplets are substantially smaller than those produced by the external mixing. Having the finer mist aids in cooling the tooth that is being drilled, and more cooling is accomplished by having the finer mist than by having the relatively large droplets produced by the prior spray devices. Additionally, since the cooling mist is produced internally of the handpiece, there is no interference with the drilling operation caused by the prior art external spray devices.

Without further elaboration, the foregoing will so fully illustrate our invention, that others may, by applying current or future knowledge, readily adapt the same for use under various conditions of service.

What is claimed as the invention is:

1. A dental handpiece comprising a turbine housing, a turbine rotatably mounted therein, a collet secured within said turbine, said collet having a plurality of jaws at the bottom thereof, said collet being externally threaded in the area of said jaws, a collet nut threadedly secured on said collet at said threads, said collet being externally tapered at the bottom thereof, said collet nut being internally tapered, with the taper of said collet nut complementing the taper of said collet, means for rotating said collet relative to said collet nut whereby the advancing of said collet nut on said collet causes the compressing of said collet jaws through the pressure of the mating of said tapered surfaces, and means on said collet nut to prevent said collet nut from becoming disengaged from said collet during the rotation of said collet.

2. The dental handpiece of claim 1 and further including means for limiting the advancement of said collet nut on said collet, thereby avoiding the crushing of said collet jaws when said tapered surfaces mate.

3. The dental handpiece of claim 2 wherein the limiting means comprise shoulders on said collet and said collet nut which are adapted to abut to avoid further advancement of said collet nut relative to said collet.

4. The dental handpiece of claim 1 wherein said collet nut has means on the outer surface thereof to prevent rotation of said collet nut while said collet is being rotated.

5. The dental handpiece of claim 4 wherein said rotation preventing means comprises a plurality of flattened faces on said collet nut.

6. The dental handpiece of claim 1 wherein the means for rotating said collet comprises slotted means at the top of said collet, said slotted means being adapted to be rotated by a tool inserted therein.

7. The dental handpiece of claim 6 wherein said turbine housing has an opening in the top thereof, and said slotted means is accessible through said opening.

8. The dental handpiece of claim 1 wherein the vertical position of said collet within said turbine housing is fixed, and said collet nut is adapted to move vertically relative to said collet.

9. The dental handpiece of claim 1 wherein said prevention means comprises an annular flange on said collet nut.

10. The dental handpiece of claim 9 wherein the bottom of said turbine housing has an opening formed therein, said collet and said collet nut projecting through said opening, said annular flange having a diameter greater than the diameter of said opening, whereby the unthreading of said collet nut relating to said collet will cause said collet nut to move downwardly, and the abutment of said annular flange against the bottom of said turbine housing adjacent said opening will cause the rotation of said collet nut to cease.

11. In combination, an air driven dental handpiece and a collet wrench therefor, said handpiece comprising a turbine housing, a turbine rotatably mounted therein, a collet secured within said turbine, said collet having a plurality of jaws at the bottom thereof, said collet being externally threaded in the area of said jaws, a collet nut threadedly secured on said collet at said threads, said collet being externally tapered at the bottom thereof, said collet nut being internally tapered, with the taper of said collet nut complementing the taper on said collet, means for rotating said collet relative to said collet nut, whereby the advancing of said collet nut on said collet causes the compressing of said collet jaws through the pressure of the mating of said tapered surfaces, means on said collet nut to prevent said collet nut from becoming disengaged from said collet during the rotation of said collet, means provided by said wrench for preventing the rotation of said collet nut and means on said collet wrench to rotate said collet relative to said collet nut.

12. The combination of claim 11 wherein said means for preventing the rotation of said collet nut comprises a plate, said plate having a slot formed therein, said slot forming a pair of jaws, said jaws being adapted to contact said collet nut, and said collet nut having flattened faces thereon, whereby the contacting of said flattened faces by said jaws prevents the rotation of said collet nut.

13. The combination of claim 12 wherein said collet nut is adapted to move vertically within said jaws.

14. The combination of claim 11 wherein the means on said collet wrench to rotate said collet comprise a shaft, said shaft having an end of non-circular cross-section, said end being adapted to be received in means on said collet having a similar cross-section, whereby the rotation of said shaft rotates said collet.

15. The combination of claim 14, and further including means secured on said shaft to aid in rotating the same.

16. The combination of claim 14 wherein said turbine housing has an opening in the top thereof, and said shaft is adapted to pass through said opening to engage the rotating means on said collet.

17. The combination of claim 11 wherein said collet wrench includes a bracket, said bracket adapted to surround said turbine housing, with the bottom of said bracket including the means to prevent the rotation of said collet nut, and the top of said bracket having the means to rotate said collet mounted thereon.

18. The combination of claim 11 wherein said prevention means comprises an annular flange on said collet nut.

19. The combination of claim 18 wherein the bottom of said turbine housing has an opening formed therein, said collet and said collet nut projecting through said opening, said annular flange having a diameter greater than the diameter of said opening, whereby the unthreading of said collet nut relating to said collet will cause said collet nut to move downwardly, and the abutment of said annular flange against the bottom of said turbine housing adjacent said opening will cause the rotation of said collet nut to cease.

* * * * *